United States Patent [19]

Baer et al.

[11] 4,158,704

[45] Jun. 19, 1979

[54] PROCESS AND COMPOSITION FOR PERMANENT WAVING

[75] Inventors: Ronald W. Baer, New City; Marvin E. Goldberg, Monsey, both of N.Y.

[73] Assignee: Revlon Inc., New York, N.Y.

[21] Appl. No.: 892,744

[22] Filed: Apr. 3, 1978

Related U.S. Application Data

[63] Continuation-in-part of Ser. No. 742,770, Nov. 18, 1976, abandoned.

[51] Int. Cl.$^2$ ............................................... A61K 7/09
[52] U.S. Cl. ............................................ 424/72; 132/7
[58] Field of Search ................................ 132/7; 424/72

[56] References Cited

FOREIGN PATENT DOCUMENTS 1119845  7/1968  United Kingdom ...................... 424/72

OTHER PUBLICATIONS

Chemical Abstracts, vol. 54 (1960), p. 13565e.

*Primary Examiner*—V. D. Turner
*Attorney, Agent, or Firm*—Leon E. Tenenbaum

[57] ABSTRACT

A process for effecting the reducing step in permanent waving by treating the hair with a thioglycolate under controlled conditions of concentration, pH, time and temperature depending upon the condition and porosity of the hair.

9 Claims, No Drawings

PROCESS AND COMPOSITION FOR PERMANENT WAVING

This application is a continuation-in-part of patent application Ser. No. 742,770, now abandoned, filed Nov. 18, 1976.

The present invention relates to permanent waving. It particularly relates to a process for permanent waving and to lotions for use in the process.

In the permanent waving of hair, the hair is treated with a reductant such as a salt of thioglycolic acid, e.g., ammonium thioglycolate, to reduce (i.e. break) the disulfide linkages in the hair proteins to sulfhydryl groups. This breakage in the disulfide linkages diminishes the rigidity of the hair proteins, leaving the hair more pliable. The hair is then set, as desired, on curlers, rods or rollers or, if preferred, the hair may be set prior to reduction. The set hair is then treated with an oxidant, such as a peroxide, which oxidizes the sulfhydryl groups to disulfide linkages thereby imparting a rigidity to the wave obtained by setting. These operations, particularly the reduction step, can be carried out at either room or elevated temperature.

Lotions for cold permanent waving contain from about 4.5 to 8.0% by weight of ammonium thioglycolate and an alkali, usually ammonium hydroxide, to maintain the pH at about 8.5 to 10.5. Lotions having a higher pH or a greater concentration of the reductant are more active than those having a lower pH or concentration. While effective permanent waving can be achieved with cold waving, there are problems with the destruction of hair because of the high pH of the reducing composition. This destruction may also be increased by the longer period of time the solution has to be kept in contact with the hair to effect the desired reduction of the disulfide linkage. The damage to or destruction of the hair is also increased when the waving is done on hair which has been previously bleached or tinted or on hair which has a porosity greater than that of normal hair.

To meet these problems the reduction is carried out at elevated temperatures (which shortens considerably the time the reductant is in contact with the hair) and at lower pH's. Ammonium thioglycolate can be used as a reductant at elevated temperatures but still requires a higher pH. More suitable reductants for use at higher temperatures, which can also be used at a lower pH, are esters of thioglycolic acid, such as the lower alkyl, hydroxy-lower alkyl, and polyhydroxy-lower alkyl esters. These esters are effective at pH's ranging from about 6.0 to 8.5 and at weight concentrations of from about 5 to 25%. Less active formulations (i.e. those having lower concentrations and/or lower pH's) are used for waving tinted, bleached or porous hair than for normal hair.

Both types of waving, the cold as well as the hot, require constant visual evaluation of the wave or curl to determine when the desired wave pattern is achieved. In cold waving this creates no special problems other than those associated with the subjectivity of the evaluation. In hot waving, there are additional problems. In hot waving a plastic cap is used to cover the hair and heat is applied by the conventional salon drier. To check the quality of the wave, the operator must remove the drier and open and then close the plastic cap. These manipulations result in the lowering of the processing temperature and the consequent prolongation of the waving process. Ultimately, with hot waving as well as with cold, the quality of the wave rests on the subjective judgment of the salon operator, and more often than not because of the subjective element the permanent waves, both hot and cold, are either underprocessed or overprocessed.

It is, accordingly, an object of the present invention to provide a process for permanent waving which will eliminate the subjective judgment of the operator in determining the conditions for waving.

It is another object of the present invention to provide a process for use in hot permanent waving in which the time and temperature variables of the reducing treatment are controlled objectively.

It is a further object of the present invention to provide a reducing composition for use in hot permanent waving, which composition is of such concentration and activity that it can be used at predetermined temperatures and for predetermined periods of time.

It is still another object of the present invention to provide a reducing composition for use in hot permanent waving, which can be used on either untreated hair or hair that has been previously permed, bleached or dyed.

Other objects will appear from the description which follows:

In accordance with this invention there is provided a process for effecting the reducing step in permanent waving which comprises treating the hair with an aqueous solution containing from about 18 to 30% by weight of an ester of thioglycolic acid and having a pH from about 6.4 to 8.3 over a predetermined period of time and at a predetermined temperature, said time and temperature being determined by the concentration of the solution, the pH of the solution, the condition of the hair and the porosity of the hair.

For solutions having a concentration of about 18 to 30% by weight of an ester of thioglycolic acid and a pH of about 6.4 to 8.3, the time will range from about 1 to 35 minutes at temperatures ranging from about 80° to 130° F., with higher temperatures and longer periods of time being used with solutions having lower concentrations of the reducing agent or lower pH's. Table I, below, illustrates time-temperatures for compositions having different ranges of concentration of reducing agent and pH. In this table the concentrations are given in weight percent, the time in minutes and the temperature in °F. The reducing agent was glyceryl thioglycolate, but other esters as discussed below, may be used in place of glyceryl thioglycolate with substantially the same results.

Table I

| Concentration of Reducing Agent | 18–22 | 23–27 | 28–30 | 18–22 | 28–30 |
|---|---|---|---|---|---|
| pH | 6.4–7.0 | 7.1–7.7 | 7.8–8.3 | 7.8–8.3 | 6.4–7.0 |
| Time | 3–35 | 2–33 | 1–30 | 2–33 | 2–33 |
| Temperature | 100–130 | 90–125 | 80–120 | 90–125 | 90–125 |

Suitable esters of thioglycolic acid for use in the process are the lower alkyl, hydroxy-lower alkyl, and polyhydroxy-lower alkyl esters wherein the alkyl group contains from 1 to 5 carbon atoms, such as, for example, ethyl thioglycolate, methyl thioglycolate, hydroxyethyl thioglycolate, hydroxypropyl thioglycolate, glyceryl thioglycolate, and the like. Preferably, we use an aqueous composition which contains from about 18 to 30% by weight of glyceryl thioglycolate and has a pH of about 6.4 to 8.3. Free thioglycolic acid in a concentration of from about 0.5 to 2.0% by weight may also be present. In addition to these ingredients the composition may contain a base such as for example, ammonium hydroxide, monoethanolamine, or triethanolamine to adjust the pH. If desired, the compositions may contain fragrances, colorants, thickening agents, surfactants, and oils. The uses of the fragrances and colorants are obvious, and the remaining materials serve to increase the viscosity of the solution, condition the hair, provide luster and shine to the hair, reduce surface tension to aid in removal of dirt and penetration, and provide emulsion stability.

Examples I to VII in the table below illustrate compositions for use in the practice of the present invention. These examples are given by way of illustration and are not to be considered as limiting.

EXAMPLES

|  | I | II | III | IV | V | VI | VII |
|---|---|---|---|---|---|---|---|
| Glyceryl Thioglycolate | 20 | 18 | 30 | 29 | 23 | 20 | 25 |
| Thioglycolic Acid | 1.5 | 1.5 | — | 1.7 | 1.5 | 2.5 | 1.0 |
| Hydrolyzed Animal Protein | — | — | — | 1.5 | 1.5 | 1.0 | 1.0 |
| POE Lauryl Alcohol 4 | — | — | — | .2 | — | — | .3 |
| POE Lauryl Alcohol 23 | — | — | — | 2.0 | — | — | 1.8 |
| POE Cetyl Alcohol 23 | — | — | — | .1 | .5 | — | — |
| Styrene Copolymer | — | — | .2 | — | .4 | — | — |
| Ammonium Hydroxide | — | — | — | 1.7 | 1.5 | — | — |
| Glycerine | — | — | — | 5.0 | 7.0 | — | 2.0 |
| Triethanolamine | 0.5 | 0.5 | 0.70 | — | — | 7.0 | — |
| Monoethanolamine | — | — | 0 | — | — | — | 12 |
| Lanolin | — | — | 2.0 | 1.0 | — | 14.0 | — |
| Glyceryl Monostearate | — | — | — | — | — | 7.0 | — |
| POE Sorbitan Monolaurate | 20 | — | — | — | — | 7.0 | — |
| Mineral Oil | — | — | — | 4.0 | — | — | 5.0 |
| Fragrance (Lemon) | — | — | — | 0.1 | .1 | .1 | .2 |
| Color (F.D. & C. Yellow #2) | — | — | — | — | — | .2 | .2 |
| Water | qs | qs | qs | qs | qs | qs | qs |
|  | 100 | 100 | 100 | 100 | 100 | 100 | 100 |
| pH | 6.5 | 6.5 | 6.5 | 7.3 | 7.4 | 7.2 | 8.2 |

In the above examples the numerical values refer to parts by weight.

POE means poly-oxyethylene and the numerical value for the POE compounds refers to the number of the oxyethylene groups in the molecule.

When the reducing step in hot permanent waving is carried out with the reducing compositions of the present invention, the operator first examines the hair to determine its porosity, resistance, and previous history (bleaching or tinting). Once this examination has been made, the operator applies a reducing solution according to the present invention, having a specified pH and specified thioglycolate concentration, for which particular solution the time - temperature parameters have been determined for the different types of hair. These parameters for each such reducing composition are provided to the operator. The operator can then set the heater at the specified temperature for a specified time.

In carrying out the process of the present invention we prefer to set the hair before applying the reductant.

We have found that we obtain a temperature control of about ±1° C. can be obtained by placing a temperature sensing device on the top of scalp and connecting the device to a time-temperature regulator. A preferred temperature sensing device for use in the process of the present invention is described in patent application Ser. No. 736,822, filed Oct. 29, 1976.

The charts on the following pages illustrate the use of the reducing compositions of the present invention.

The concentrations are given as percent by weight and the times are given in minutes.

CHART #1

(Thioglycolate Concentration)
Glyceryl thioglycolate (23.5 ± 0.2) and
Thioglycolic acid (1.5 ± 0.1)
pH 6.8 ± 0.1

| HAIR TYPE | DEGREE OF POROSITY | TEMP. ± 1°F. | TIME IN MINUTES ± 10 SECONDS |
|---|---|---|---|
| Bleached | Highly – Slightly | 85 | 3 |
|  | Very Slightly – None | 85 | 5 |
| Tinted | Highly – Normal | 95 | 7 |
|  | Normal – Very Slight | 95 | 8.5 |
|  | Very Slight – None | 95 | 10 |
| Normal | Highly – Normal | 115 | 12.5 |
|  | Normal – Very Slight | 115 | 14.25 |
|  | Very Slight – None | 115 | 16 |
| Resistant | Highly – Normal | 125 | 20 |
|  | Normal – Very Slight | 125 | 22 |
|  | Very Slight – None | 125 | 24 |

CHART #2

(Thioglycolate Concentration)
Glyceryl Thioglycolate 18.0 ± 0.4
pH 6.4 ± .2

| HAIR TYPE | DEGREE OF POROSITY | TEMP. ± 1°F. | TIME IN MINUTES ± 10 SECONDS |
|---|---|---|---|
| Bleached | Highly – Slightly | 90 | 5 |
|  | Very Slightly – None | 90 | 7 |
| Tinted | Highly – Normal | 100 | 9 |
|  | Normal – Very Slight | 100 | 11 |
|  | Very Slight – None | 100 | 13 |
| Normal | High – Normal | 120 | 15 |
|  | Normal – Very Slight | 120 | 17 |
|  | Very Slight – None | 120 | 19 |
| Resistant | Highly – Normal | 130 | 23 |
|  | Normal – Very Slight | 130 | 25 |
|  | Very Slight – None | 130 | 27 |

CHART #3

(Thioglycolate Concentration)
Thioglycolic Acid (0.5 ± 0.1) and
Glyceryl Thioglycolate (20.0 ± 0.3)
pH 7.3 ± .1

| HAIR TYPE | DEGREE OF POROSITY | TEMP. ± 1°F. | TIME IN MINUTES ± 10 SECONDS |
|---|---|---|---|
| Bleached | Highly – Slightly | 80 | 2 |
| | Very Slightly – None | 80 | 3 |
| Tinted | Highly – Normal | 90 | 4 |
| | Normal – Very Slight | 90 | 5 |
| | Very Slight – None | 90 | 6 |
| Normal | Highly – Normal | 110 | 8 |
| | Normal – Very Slight | 110 | 9 |
| | Very Slight – None | 110 | 10 |
| Resistant | Highly – Normal | 120 | 12 |
| | Normal – Very Slight | 120 | 13 |
| | Very Slight – None | 120 | 14 |

We claim:

1. A process for effecting the reducing step in permanent waving which comprises treating the hair with an aqueous solution containing from about 18 to 30% by weight of an ester of thioglycolic acid, said ester being selected from the group consisting of lower alkyl, hydroxy-lower alkyl and glyceryl esters, and having a pH of about 6.4 to 8.3, for about 1 to 35 minutes at a temperature from about 80° to 130° F., with the time and temperature parameters being selected as follows:

| Concentration of Reducing Agent in % by weight | 18–22 | 23–27 | 28–30 | 18–22 | 28–30 |
|---|---|---|---|---|---|
| pH | 6.4–7.0 | 7.1–7.7 | 7.8–8.3 | 7.8–8.3 | 6.4–7.0 |
| Time in Minutes | 3–35 | 2–33 | 1–30 | 2–33 | 2–33 |
| Temp. in °F. | 100–130 | 90–125 | 80–120 | 90–125 | 90–125 |

2. A process according to claim 1 wherein the ester is a glyceryl ester.

3. A process according to claim 2 wherein the concentration of the ester is about 18 to 22% by weight, the pH is about 6.4 to 7.0, the time range is about 3 to 35 minutes and the temperature is about 100° to 130° F.

4. A process according to claim 2 wherein the concentration is about 23–27% by weight, the pH is about 7.1 to 7.7, the time range is about 2 to 33 minutes, and the temperature is about 90° to 125° F.

5. A process according to claim 2 wherein the concentration is about 28 to 30% by weight, the pH is about 7.8 to 8.3, the time range is about 1 to 30 minutes, and the temperature is about 80° to 120° F.

6. A process according to claim 2 wherein the aqueous solution contains about 0.5 to 2.0% by weight of thioglycollic acid.

7. A process according to claim 6 wherein the solution has about 23.5% by weight of glyceryl thioglycolate, about 1.5% by weight of thioglycollic acid, a pH of about 6.8, and the times and temperatures for different types of hair are as follows:

| HAIR TYPE | DEGREE OF POROSITY | TEMP. + 1° C. | TIME IN MINUTES ± 10 SECONDS |
|---|---|---|---|
| Bleached | Highly – Slightly | 85 | 3 |
| | Very Slightly – None | 85 | 5 |
| Tinted | Highly – Normal | 95 | 7 |
| | Normal – Very Slight | 95 | 8.5 |
| | Very Slight – None | 95 | 10 |
| Normal | Highly – Normal | 115 | 12.5 |
| | Normal – Very Slight | 115 | 14.25 |
| | Very Slight – None | 115 | 16 |
| Resistant | Highly Normal | 125 | 20 |
| | Normal – Very Slight | 125 | 22 |
| | Very Slight – None | 125 | 24 |

8. A process according to claim 2 wherein the solution has about 18.0% by weight of glyceryl thioglycolate, a pH of about 6.4, and the times and temperatures for different types of hair are as follows:

| HAIR TYPE | DEGREE OF POROSITY | TEMP. ± 1°F. | TIME IN MINUTES ± 10 SECONDS |
|---|---|---|---|
| Bleached | Highly – Slightly | 90 | 5 |
| | Very Slightly – None | 90 | 7 |
| Tinted | Highly – Normal | 100 | 9 |
| | Normal – Very Slight | 100 | 11 |
| | Very Slight – None | 100 | 13 |
| Normal | Highly – Normal | 120 | 15 |
| | Normal – Very Slight | 120 | 17 |
| | Very Slight – None | 120 | 19 |
| Resistant | Highly – Normal | 130 | 23 |
| | Normal – Very Slight | 130 | 25 |
| | Very Slight – None | 130 | 27 |

9. A process according to claim 6 wherein the solution has about 20.0% by weight of glyceryl thioglycolate, about 0.5% by weight of thioglycolic acid, a pH of about 7.3, and the times and temperatures for different types of hair are as follows:

| HAIR TYPE | DEGREE OF POROSITY | TEMP. ± 1°F. | TIME IN MINUTES ± 10 SECONDS |
|---|---|---|---|
| Bleached | Highly – Slightly | 80 | 2 |
| | Very Slightly – None | 80 | 3 |
| Tinted | Highly – | 90 | 4 |

| HAIR TYPE | DEGREE OF POROSITY | TEMP. ± 1°F. | TIME IN MINUTES ± 10 SECONDS |
|---|---|---|---|
|  | Normal |  |  |
|  | Normal – Very Slight | 90 | 5 |
|  | Very Slight – None | 90 | 6 |
| Normal | Highly – Normal | 110 | 8 |
|  | Normal – Very Slight | 110 | 9 |
|  | Very Slight – None | 110 | 10 |
| Resistant | Highly – Normal | 120 | 12 |
|  | Normal – Very Slight | 120 | 14 |
|  | Very Slight – None | 120 | 14 |

* * * * *